United States Patent [19]

Worden

[11] Patent Number: 5,234,235
[45] Date of Patent: Aug. 10, 1993

[54] CONNECTION APPARATUS

[75] Inventor: Raymond D. Worden, Houston, Tex.

[73] Assignee: Ruska Laboratories, Inc., Houston, Tex.

[21] Appl. No.: 982,796

[22] Filed: Nov. 30, 1992

[51] Int. Cl.⁵ .................... F16L 25/00; F16L 35/00
[52] U.S. Cl. .................. 285/334.4; 285/342; 285/353; 285/357
[58] Field of Search ............ 285/334.4, 342, 348, 285/911, 369, 354, 375, 341, 343, 334.3, 357

[56] References Cited

U.S. PATENT DOCUMENTS

| | | | |
|---|---|---|---|
| 3,992,043 | 11/1976 | Whitley | 285/342 |
| 4,281,679 | 8/1981 | Stearns | 285/342 |
| 4,529,230 | 7/1985 | Fatula, Jr. | 285/911 |
| 4,669,756 | 6/1987 | Cassaday et al. | 285/369 |
| 4,690,437 | 9/1987 | Anderson, Jr. | 285/911 |
| 4,787,656 | 11/1988 | Ryder | 285/911 |
| 4,991,883 | 2/1991 | Worden | 285/334.4 |
| 5,163,722 | 11/1992 | Worden | 285/375 |

FOREIGN PATENT DOCUMENTS 812640  5/1969  Canada ................ 285/334.4
1054294  4/1959  Fed. Rep. of Germany ...... 285/911

Primary Examiner—Eric K. Nicholson
Attorney, Agent, or Firm—Browning, Bushman, Anderson & Brookhart

[57] ABSTRACT

An improved apparatus for connecting first and second conduits, which may be capillary columns, having first and second bores, respectively, to provide communication between the first and second bores for high temperature operation over wide variations in temperature. A monolithic fused quartz seating element is removably insertable into a seating chamber of a base that may be comprised of steel or other metal. The monolithic fused quartz seating element may be cylindrical and have frustoconical surfaces defining first and second receiving formations. First and second slidable followers biased by first and second quartz springs apply pressure against first and second ferrules to seal between the first and second receiving formations, and the first and second conduits, respectively.

11 Claims, 1 Drawing Sheet

CONNECTION APPARATUS

BACKGROUND OF THE INVENTION

1. Field of the Invention

The present invention relates to an improved apparatus for effecting gas-tight communications between first and second members having bores for the passage of fluid. More particularly, the present invention relates to an improved connection having a monolithic sealing element with distinct ferrule forming and ferrule biasing engagement surfaces for connecting first and second tubular members.

2. Description of the Background

There are numerous types of analytical instrumentation used in laboratories, chemical and refining plants and the like, which require high temperature connection of a first tubular member through which is transported a fluid, such as a gas, to a second tubular member.

Exemplary examples of such connections are shown in U.S. Pat. No. 4,991,883 ('883) and U.S. Pat. No. 5,163,722 ('722) to R. D. Worden, which are incorporated herein by reference. The connection shown in the '883 patent provides a fluid tight connection for operation over wide temperature ranges and high temperatures that subject the mechanical components of this connection to considerable expansion and contraction. In a preferred embodiment of the invention disclosed in the '883 patent, a fused quartz spring is used as a biasing element to maintain a constant biasing force on a sealing ferrule. The sealing ferrule seals between an inner conduit containing a fluid and an outer sealing surface.

On occasion, it is desirable to use a fluid carrying conduit that is undersize with respect to the sealing ferrule. While a quartz spring provides ample force to maintain sealing pressure during wide temperature variations, such a spring may not be strong enough to make an initial seal with an undersize conduit. The 722' patent shows an apparatus that creates an initial seal by applying force to a follower. After forming an initial seal, pressure is maintained against the follower by the quartz spring.

A continuing problem with high temperature connectors of the type under consideration is the high cost and fragile nature of components often associated with such connectors. The connectors operate at high temperatures in excess of 400° C. They also experience wide temperature swings in excess of 600° C. Additionally, they must be chemically inert to be of practical value. Thus, fused quartz is often the only practical material of which the base portion of these connectors can be formed. However, fused quartz is relatively fragile as compared with steel, for instance. Moreover, fused quartz structures tend to be expensive. While fused quartz is generally impervious to most materials, at the temperatures of operation the fused quartz exposed surfaces may become coated or fused with other materials, e.g., the components passing through the tubular member. When damage of any type occurs, the relatively expensive connector must be replaced. It is frequently necessary to heat the quartz components thereby requiring substantial time and heat energy to bring the structure to the desired temperature and maintain or alter the temperature thereof as required.

Consequently, a need exists for improvements in high temperature connections that experience wide variations temperatures. Those skilled in the art have long sought and will appreciate the novel features of the present invention that solves these problems.

SUMMARY OF THE INVENTION

An object of the present invention is to provide an improved, high temperature connector with a replaceable monolithic seating element for use in a connector base element that may utilize sturdy aluminum or steel construction.

Another object of the present invention is to provide a readily replaceable seat for connecting two capillary columns each having a ferrule sealing element.

A further object of the present invention is to provide for independent contact surfaces to apply pressure against a ferrule sealing element for initial sealing and subsequent maintenance of a seal during contraction and expansion of components over wide temperature changes.

An additional object of the present invention is to provide a high temperature base connector to which multiple connectors may sealingly engage.

The above and other objects of the present invention will become apparent from the drawings, the description herein and the appended claims.

A preferred embodiment of the present invention provides a high temperature, gas-tight connection between a first conduit having a first bore and a second conduit having a second bore thereby allowing communication between the first and second bores. The apparatus includes first and second ferrules received on first and second respective conduits. The ferrules each include a deformable portion for sealing. First and second followers are disposed to be slidably engageable with the first and second ferrules, respectively. The followers each have a passageway through which the respective conduits extend. First and second biasing means are operative to urge the respective followers against the respective ferrules. Additionally, a monolithic seating element is disposed within a seating chamber of a base element. The monolithic seating element has first and second surfaces defining first and second receiving formations for the respective ferrules to effect sealing between the respective conduits and the respective receiving formations. The respective receiving formations are in communication through a passageway in the seating element.

BRIEF DESCRIPTION OF THE DRAWINGS

Other features and intended advantages of the present invention will be readily apparent by the references to the following detailed description in connection with the accompanying drawing, wherein.

While the invention will be described in connection with the presently preferred embodiment, it will be understood that it is not intended to limit the invention to this embodiment. On the contrary, it is intended to cover all alternatives, modifications and equivalents as may be included in the spirit of the invention and as defined in the appended claims.

DETAILED DESCRIPTION OF THE PREFERRED EMBODIMENTS

Figure 1:
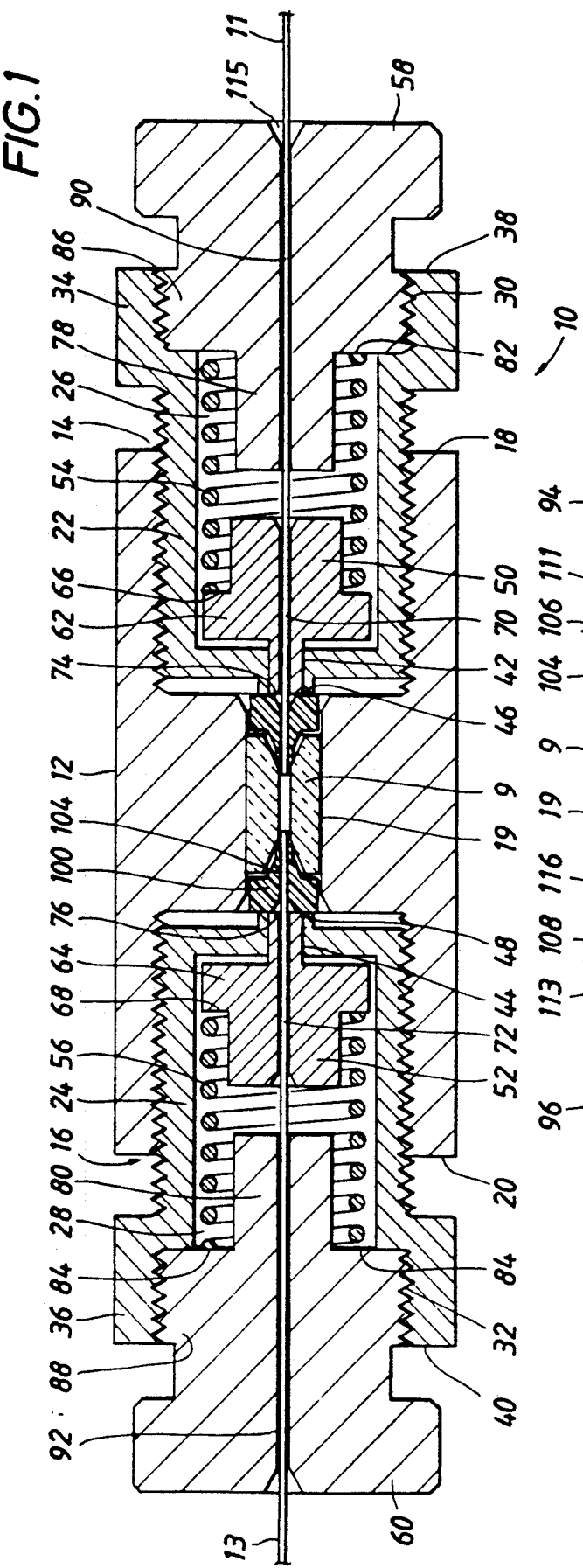
FIG. 1 is a side elevational view, in section, showing an improved connector in accord with the present invention.

The present invention combines and improves on the advantages of a springbiased high temperature connector in a new, novel connector which employs a removably insertable seating element and independent surfaces separately engageable with a sealing ferrule. The main internal components of the improved high temperature connection 10, for connecting conduits 11 and 13, are seen in FIG. 1. The apparatus of the present invention may be used for connection of various size conduits 11 and 13 including relatively small capillary columns having internal diameters ranging from 0.2–0.8 mm.

In the presently preferred embodiment, base 12 includes two threaded ports 14 and 16 on opposing base sides 18 and 20, respectively. Additional ports could also be incorporated into base 12 as discussed hereinafter. Base 12 is preferably formed from aluminum, steel, or other metallic material to provide strength at a relatively low cost to connector 10. Seating chamber 19 interconnects threaded ports 14 and 16. Base 12 may also include heating elements (not shown) for quickly heating and/or controlling the temperature of the relatively diminutive, with respect to base 12, monolithic seating element 9. Although seating element 9 is preferably comprised of fused quartz, it may also be comprised of a glass-like material or other substances as described subsequently. Glass-like materials are generally meant to include ceramics that are typically are comprised of silica.

On either side of base 12, threaded nozzles 22 and 24 engage complementary threaded ports 14 and 16, respectively. Threaded nozzles 22 and 24 include internal cylindrical bores 26 and 28 that have smooth wall surfaces. Flange portions 34 and 36 of the nozzles surround outer threaded bore portions 30 and 32 that extend through nozzle end walls 38 and 40, respectively. Nozzles 22 and 24 include outer extensions 46 and 48 through which extend cylindrical bores 42 and 44, respectively. It is appreciated that outer extensions 46 and 48 are moveable into and out of bore 14 and 16 as nozzles 22 and 24, respectively, are rotated.

Disposed within nozzles 22 and 24 are followers 50 and 52, quartz seal compression springs 54 and 56, and spring pressure adjusting nuts 58 and 60, respectively.

Followers 50 and 52 are slidably disposed within bores 26 and 28. Each follower includes a flange portion 62 and 64, respectively, that effectively centralizes the respective follower in respective bores 26 and 28. The flange portions 62 and 64 have thereon spring engaging surfaces 66 and 68. Centrally disposed apertures 70 and 72 extend through the respective followers. Conduits 11 and 13 may be disposed within apertures 70 and 72. Inner boss extensions 74 and 76 extend through bores 42 and 44 of outer extensions 46 and 48. It will be appreciated that inner boss extensions 74 and 76 may be biased with constant pressure as outer extensions 46 and 48 separately move into and out of bores 26 and 28 of base 12.

Quartz seal compression springs 54 and 56 encircle a portion of the respective followers that, if appropriately sized, may provide centralization of the springs with respect to the followers. The quartz seal compression springs engage respective spring engagement surfaces 66 and 68 on the respective followers to apply a biasing pressure. While other types of springs could also be used, the quartz spring may be chosen for constant biasing pressure over a wide range of temperatures. Other springs may be used if a constant biasing pressure is not critical, to reduce cost, or if the desired biasing pressure is greater than the biasing pressure obtainable from a quartz spring of similar dimensions.

Spring pressure adjusting nuts 58 and 60 have respective body portions 78 and 80 that may be sized to centralize respective quartz seal compression springs. Centrally disposed apertures 90 and 92 extend through spring pressure adjusting nuts 58 and 60, respectively, for use with conduits 11 and 13. Spring engagement surfaces 82 and 84 on respective threaded flanges 86 and 88 may be utilized to adjust biasing pressure. It will be appreciated that biasing pressure created by the quartz seal compression springs can be adjusted by rotating threaded flanges 86 and 88 using spring pressure adjusting nuts 58 and 60 with respect to threaded bores 30 and 32 of nozzles 22 and 24, respectively. Thus, biasing pressure may be applied to respective inner boss extensions 74 and 76 separately from any biasing or deforming pressure that may be applied via outer extensions 46 and 48.

Figure 2:
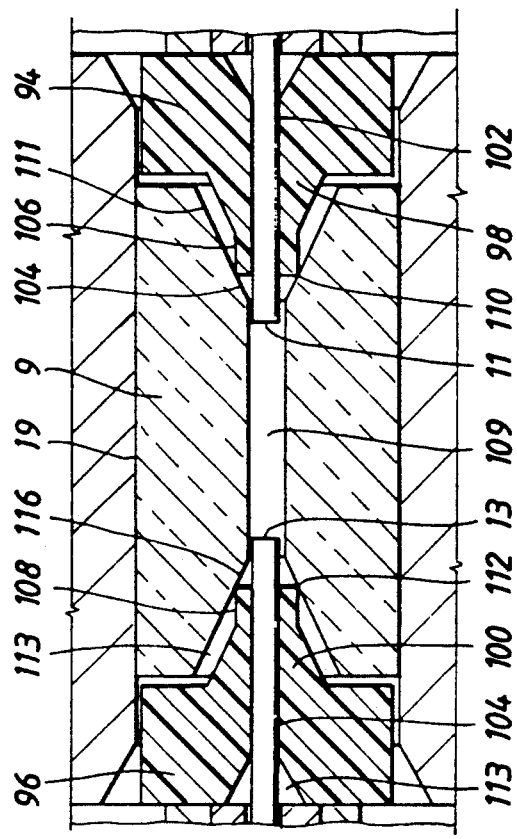
FIG. 2 is an enlarged view, in section, of a monolithic seating element with engaging ferrules in accord with the present invention.

Outer extensions 46 and 48 apply pressure against respective ferrule flange portions 94 and 96 and thereby with seating element 9. Ferrule flange portions 94 and 96 limit movement of the ferrules and seating element 9 after contact with end portions thereof. Ferrules 98 and 100 include deformable portions that seal with sealing surfaces on monolithic seating element 9. The term "deformable" as used herein refers to a material which, under compression, deforms to the extent necessary to achieve a gas-tight seal between the ferrule and the engaged surface or surfaces and conduits 11 and 13. Respective centrally disposed internal apertures 102 and 104 (FIG. 2) may include deformable portions for sealing conduits 11 and 13 even if the conduits are slightly undersize with respect the apertures. In a preferred embodiment, ferrules 98 and 100 have deformable cylindrical portions 106 and 108 (See FIG. 2) that make line contact along lines 110 and 112 for gas-tight sealing with a frustoconical receiving formation described subsequently. More specifically cylindrical portions 106 and 108 include a circular transverse cross-section that engages a frustoconical receiving formation substantially in line contact in the locus a deformable portion of ferrules 98 and 100. Deformable cylindrical portions 106 and 108, or other deformable portions of ferrules 98 and 100 may also be used to form the seal around conduits 11 and 13.

Disposed within cylindrical seating chamber 19 is monolithic seating element 9. Monolithic glass-like seating element 9 is typically comprised of fused quartz or other glass-like materials to provide an inert material for use at high temperatures and over wide variations in temperature. Seating element 9 is preferably cylindrical and mates to seating chamber 19. For this reason, it will be appreciated that sealing element 9 is slidably disposed within cylindrical seating chamber 19 and is therefore easily replaceable as may be necessary, for instance, due to breakage or chemical contamination. The fact that monolithic seating element 9 is slidable allows it to self-adjust its position between ferrules 98 and 100 as required to approximately equal pressure on both ends thereof. Thus, quartz sealing compression springs 54 and 56 interact with each other for sealing purposes due to the slidable nature of monolithic seating element 9. Seating element 9 has frustoconical surfaces 111 and 113 formed therein interconnected by bore 109.

The frustoconical surfaces generally define corresponding receiving surfaces in the locus of 114 and 116 for forming gas-tight seals through engagement with deformable cylindrical portions 106 and 108.

While monolithic seating element 9 is shown for use with two co-axial nozzles having corresponding conduits to be connected, it may also connect nozzles or ferrules disposed at right angles or other angles with respect to each other. It may be used with more than two conduits. For instance, monolithic seating element 9 could have a Y-shaped internal passageway or a T-shaped internal passageway for use with additional ports in base 12. This construction allows for multiple frustoconical receiving surfaces. Base 12 may also be part of a larger vessel whereby only one threaded port and ferrule may be provided. The construction of the seating element 9 could allow replacement through a passageway transverse to the conduits to be connected or a passageway generally parallel to the conduits as shown.

In operation, monolithic seating element 9 is inserted into cylindrical seating chamber 19 if it is not already present. Since monolithic seating element 9 is slidable, it is self adjusting between ferrules 98 and 100. Other arrangements could also be used for securing element 9. For instance, a transverse passageway (not shown) through which seating element 9 may be movable could include stop surfaces for locking element 9 in place.

Conduits 11 and 13, which may be capillary columns, are then threaded through respective components as shown and the various components are connected to base 12. Due to the small size of capillary columns, it is preferable to have beveled or frustoconical inlets, such as beveled inlet 115 (shown as conduit 11 enters connection apparatus 10) to aid in threading capillary columns. It may be desirable to adjust biasing pressure applied to ferrule followers 50 and 52 prior to insertion of corresponding nozzles 22 and 24 into base 12. As noted, the biasing pressures will interact due to the slidable mounting of seating element 9. Spring pressure adjusting nuts 58 and 60 are used for this purpose. After assembly as shown in FIG. 1, a gas-tight connection may then be effected between conduits 11 and 13 by applying pressure to ferrules 98 and 100 via flange 34 and 36.

The present invention allows pressure to applied to each ferrule by separate concentrically or annularly disposed inner boss extensions 74, 76 and outer extensions 46, 48 respectively. Generally, pressure is applied to the ferrules for two separate reasons. Initial pressure may be applied to deform the ferrule for sealing with seating element 9 and with conduits 11 and 13. Biasing pressure is applied to the ferrules to maintain the seal as temperatures vary and the components expand and contract accordingly. The use of two surfaces for applying the pressures eliminates any interplay between the ferrule follower and extensions 46 and 48. Flanges 34 and 36 rotate to apply pressure through extensions 46 and 48 to deform the ferrules thereby effecting the initial gas-tight sealing with seating element 9 and conduits 11 and 13. The spring loaded biasing pressure corrects for expansion and contractions that may occur especially if wide temperature swings are anticipated. The initial gas-tight seal effected by rotating flanges 34 and 36 may not be adequate to maintain the seal without the biasing pressure to correct for expansion and contractions of material in the connector 10. On the other hand, the spring loaded biasing pressure administered through inner boss extensions 74 and 76 may not be adequate to effect the initial seal between the ferrules, conduits and seating element 9. This may be especially true if the conduits are undersize with respect to the ferrules.

While seating element 9 has been discussed in terms of glass-like material or fused quartz, other materials may also be used. For instance, when it is not necessary to have a material as inert as fused quartz, then materials including metals could be used for manufacture of seating element 9. Other specific materials may also be suitable for certain configurations and fluids or gasses. Cost may also be a factor to be considered in selection of material for a seating element, especially where the demands on the selected material will not be extreme.

The aspect of line contact sealing is discussed more thoroughly in exemplary U.S. Pat. Nos. 4,991,883 and U.S. Pat. No. 5,163,722 that, as previously stated, are incorporated herein by reference.

The foregoing description of the invention has been directed in primary part to particular preferred embodiments in accordance with the requirements of the patent statutes and for purposes of illustration. It will be apparent, however, to those skilled in the art that many modifications and changes may be made without departing form the scope and spirit of the invention. Therefore, the invention is not restricted to the preferred embodiment illustrated but covers all modifications that may fall within the scope of the following claims.

What is claimed is:

1. A high temperature, gas tight connection for connecting a first conduit having a first bore to a second conduit having a second bore allowing communication between said first and second bores comprising:
    a base having a seating chamber therein;
    a first ferrule received on said first conduit, a second ferrule received on said second conduit, each of said first and second ferrules having a first end and a second end;
    a first follower for engaging said first ferrule, a second follower for engaging said second ferrule, each of said first and second followers having a passageway therethrough, said first and second conduits extending through said passageways in said first and second followers, respectively;
    first and second biasing means operative to urge said first and second followers against said first ends of said first and second ferrules, respectively; and
    a monolithic seating element removably disposed in said seating chamber, said seating element having a first surface defining a first receiving formation for receiving said second end of said first ferrule and a second surface defining a second receiving formation for receiving said second end of said second ferrule, said first and second receiving formations being in open communication with one another through said seating element, each of said first and second ferrules having a portion received in said first and second receiving formations, respectively, which is sufficiently deformable to effect sealing engagement with said seating element and said first and second conduits, respectively, when said first and second ferrules are urged into said first and second receiving formations, respectively.

2. The apparatus of claim 1, further comprising:
    a first frustoconical surface on said seating element defining said first receiving formation and a second frustoconical surface on said seating element defining said second receiving formation, each of said second ends of said first and second ferrules having a portion that is circular when viewed in transverse cross-section such that when said second ends of said first and second ferrules are urged into said first and second receiving formations by said first and second biasing means, respectively, said first ferrule engages said first frustoconical surface in substantially line contact and said second ferrule engages said second frustoconical surface in substantially line in contact, said sufficiently deformable portion of said first and second ferrules being in the locus of said substantially line contact of said first and second ferrules and said respective first and second frustoconical surfaces.

3. The apparatus of claim 1, further comprising:
ferrule deforming means independent of said first and second followers for deforming said deformable portion of said first and second ferrules to effect an initial sealing engagement independently from said from said first and second followers.

4. The apparatus of claim 1, wherein:
said monolithic seating element is slidably mounted within said seating chamber for slidable contact between said first and second ferrules.

5. The apparatus of claim 1, wherein:
said monolithic seating element is comprised of fused quartz.

6. The apparatus of claim 1, wherein:
said base is comprised of a metallic material.

7. The apparatus of claim 1, wherein:
said first and second receiving formations are substantially co-axial.

8. The apparatus of claim 1, wherein:
said first and second conduits comprise first and second capillary columns respectively.

9. An apparatus for connecting a first conduit having a first bore to a second conduit having a second bore to provide communication between said first and second bore, comprising:
a base having a seating chamber therein;
a first ferrule received on said first conduit, said first ferrule having a first end and a second end;
a first follower for engaging said first ferrule, said first follower having a passageway therethrough, said first conduit extending through said passageway;
first biasing means operative to urge said first follower against said first end of said first ferrule;
a first surface within said seating chamber defining a first receiving formation for receiving said second end of said first ferrule, said first ferrule having a portion received in said first receiving formation that is sufficiently deformable to effect sealing engagement with said seating element and said first conduit when said first ferrule is urged into said first receiving formation; and
a first ferrule deforming means independent of said first follower for deforming said deformable portion of said first ferrule to effect an initial sealing engagement independently from said first follower.

10. The apparatus of claim 9, further comprising:
a glass-like seating element disposed in said seating chamber of said base, said glass-like seating element including said first receiving formation for said first ferrule.

11. The apparatus of claim 10, further comprising:
a second ferrule received on said second conduit, said second ferrule having a first end and a second end;
a second follower slidably engageable with a second ferrule, said second follower having a passageway therethrough, said second conduit extending through said passageway;
second biasing means operative to urge said second follower against said first end of said second ferrule;
said glass-like seating element having a surface defining second receiving formation for said second ferrule, said second ferrule having a portion received in said second receiving formation that is sufficiently deformable to effect sealing engagement with said seating element and said second conduit when said second ferrule is urged into said second receiving formation; and
a second ferrule deforming means independent of said second follower for deforming said deformable portion of said second ferrule to effect an initial sealing engagement independently from said second follower.

* * * * *